US010980714B2

(12) United States Patent
Agrawal et al.

(10) Patent No.: US 10,980,714 B2
(45) Date of Patent: Apr. 20, 2021

(54) CLEANSING SCRUB COMPOSITION

(71) Applicant: L'OREAL, Paris (FR)

(72) Inventors: Tanu Agrawal, Mumbai (IN); Shoibal Pattanaik, Mumbai (IN)

(73) Assignee: L'Oreal ( * ) Notice: Subject to any disclaimer, the term of this patent is extended or adjusted under 35 U.S.C. 154(b) by 23 days.

(21) Appl. No.: 15/569,072

(22) PCT Filed: May 6, 2016

(86) PCT No.: PCT/EP2016/060236
§ 371 (c)(1),
(2) Date: Oct. 24, 2017

(87) PCT Pub. No.: WO2016/177902
PCT Pub. Date: Nov. 10, 2016

(65) Prior Publication Data
US 2018/0133117 A1 May 17, 2018

(30) Foreign Application Priority Data
May 7, 2015 (IN) .......................... 1822/MUM/2015

(51) Int. Cl.
A61K 8/04 (2006.01)
A61Q 19/10 (2006.01)
A61K 8/46 (2006.01)
A61K 8/81 (2006.01)
A61K 8/73 (2006.01)
A61K 8/25 (2006.01)

(52) U.S. Cl.
CPC ............... A61K 8/042 (2013.01); A61K 8/25 (2013.01); A61K 8/463 (2013.01); A61K 8/73 (2013.01); A61K 8/733 (2013.01); A61K 8/736 (2013.01); A61K 8/8152 (2013.01); A61Q 19/10 (2013.01); A61K 2800/28 (2013.01); A61K 2800/412 (2013.01)

(58) Field of Classification Search
CPC ............ A61K 8/042; A61K 8/73; A61K 8/25
See application file for complete search history.

(56) References Cited

U.S. PATENT DOCUMENTS

| 6,066,613 | A  | * | 5/2000 | Tsaur ................... B01J 13/0065 510/403 |
| 6,391,288 | B1 | * | 5/2002 | Miyazawa ........... A61K 8/0208 424/400 |
| 6,467,699 | B1 | * | 10/2002 | Vorlop ..................... B01J 2/06 239/1 |
| 6,533,873 | B1 |   | 3/2003 | Margosiak et al. |
| 7,182,537 | B2 | * | 2/2007 | Policicchio .......... C11D 17/049 401/138 |
| 8,062,649 | B2 | * | 11/2011 | Asmus .................... A61P 31/00 424/405 |
| 2003/0072805 | A1 | * | 4/2003 | Miyazawa ........... A61K 8/0212 424/489 |
| 2003/0198654 | A1 |   | 10/2003 | Palazzolo |
| 2006/0211588 | A1 | * | 9/2006 | Fonolla Moreno ...... A61K 8/39 510/126 |
| 2008/0035174 | A1 | * | 2/2008 | Aubrun-Sonneville ..................... A61K 8/0208 134/18 |
| 2010/0323996 | A1 | * | 12/2010 | Ute ....................... A61Q 17/005 514/164 |
| 2011/0088711 | A1 | * | 4/2011 | Bonafos ............... A61K 8/0208 132/200 |
| 2011/0223215 | A1 | * | 9/2011 | Mason .................. A61K 9/0014 424/400 |
| 2012/0077880 | A1 |   | 3/2012 | Quan et al. |
| 2013/0156831 | A1 | * | 6/2013 | Matsuo ..................... C08L 5/00 424/401 |
| 2015/0342848 | A1 | * | 12/2015 | Bhushan ................ A01N 57/12 424/411 |
| 2018/0133117 | A1 | * | 5/2018 | Agrawal .................. A61K 8/73 |

FOREIGN PATENT DOCUMENTS

| CN | 2013120095 | | 7/2014 | |
| EP | 0829259 | | 3/1998 | |
| JP | H10-226621 | | 8/1998 | |
| JP | 2001-097819 | | 4/2001 | |
| JP | 2001097819 | A * | 4/2001 | |
| JP | 2001-187710 | | 7/2001 | |
| JP | 2002-363535 | | 12/2002 | |
| JP | 2005314362 | | 11/2005 | |
| JP | 2006-182735 | | 7/2006 | |
| JP | 2007-302563 | | 11/2007 | |
| JP | 2007302563 | A * | 11/2007 | |
| JP | 2009-275012 | | 11/2009 | |
| JP | 2010-013428 | | 1/2010 | |
| JP | 2011-088832 | | 5/2011 | |
| JP | 2013-103920 | | 5/2013 | |
| JP | 5570696 | | 8/2014 | |
| KR | 10-20090008544 | | 1/2009 | |
| WO | 2006085907 | | 8/2006 | |
| WO | WO-2006085907 | A2 * | 8/2006 | ............. A01N 25/04 |
| WO | 2008064162 | | 5/2008 | |
| WO | WO 2008149562 | | 11/2008 | |
| WO | WO 2014171738 | | 10/2014 | |
| WO | WO-2016177902 | A1 * | 11/2016 | ............. A61K 8/463 |

OTHER PUBLICATIONS

Mintel; Jan. 1, 2014 (Jan. 1, 2014), "Splash Body Wash".
Mintel; Mar. 1, 2010 (Mar. 1, 2010), "Exfoliating Face Wash".

* cited by examiner

Primary Examiner — Liam J Heincer
Assistant Examiner — M. Reza Asdjodi
(74) Attorney, Agent, or Firm — Michael Rubin; Rudy J. Ng; Bozicevic, Field & Francis llp

(57) ABSTRACT

The present invention relates to an aqueous composition comprising (i) at least hydrogel beads comprising 2 gelling agents chosen from (hetero)polysaccharides, (ii) at least one foaming surfactant, and (iii) at least anacrylic copolymer of acrylic acid and C10-C30 alkyl acrylate. The present invention further relates to the use of said composition as a cleansing scrub composition of the skin.

16 Claims, No Drawings

CLEANSING SCRUB COMPOSITION

The present invention relates to cleansing scrub compositions comprising hydrogel beads, a foaming surfactant and a specific acrylic copolymer. The present invention also relates to the use of said composition as scrub composition for the skin.

Scrubbing compositions aim at making the skin softer and better prepared for the application, for example, of skin care products or of makeup. Most of the traditional scrubbing compositions on the market contain scrubbing particles, such as polyethylene powders, vegetal powders, silica, polyamide, cellulose beads, and microcrystalline wax. These particles dispersed in aqueous medium are distinctly visible.

Commercially available scrub compositions are often harsh, provoke skin irritation and then cannot be used daily.

The aim of the present invention is to provide a cleansing scrub composition for the skin, preferably for the face or the body, that is translucent and wherein the scrubbing particles are not visually distinct. Then, the consumer has a perception of mildness, freshness and purity.

By "translucent", it is meant that the composition is nor opaque nor opalescent and is in a form enabling the passing through of the light without distinction of shapes.

Another aim of the present invention is to provide a cleansing scrub composition that is stable.

In the sense of the present invention, "stable" means that the composition does not undergo visual changes after 2 weeks, preferably 1 month, of storage at 37° C., and that the beads remain suspended at these conditions of storage.

The applicant surprisingly found these aims are achieved by the use of an aqueous composition comprising particular beads containing at least 2 gelling agents chosen among (hetero)polysaccharides, a foaming surfactant and a specific acrylic copolymer.

Advantageously, the cleansing scrub composition according to the invention is also pleasant on application, non-tacky, and leaves a clean and fresh feel after use.

Advantageously, the composition is mild, gentle and soft when applied on the skin and has no irritating effect. Advantageously, the composition of the invention can be used daily.

Advantageously, the composition is biodegradable and environmentally friendly.

The invention relates to composition comprising in an aqueous medium (i) hydrogel beads comprising at least 2 gelling agents chosen among (hetero)polysaccharides, (ii) at least a foaming surfactant and (iii) an acrylic copolymer as described hereafter.

The invention further relates to the process for cleansing the skin, preferably the face or the body, comprising applying to the skin a composition comprising, in an aqueous medium, (i) hydrogel beads comprising at least 2 gelling agents chosen from (hetero)polysaccharides, (ii) at least a foaming surfactant and (iii) an acrylic copolymer as described below.

The invention further relates to the use of composition comprising, in aqueous medium, (i) hydrogel beads comprising at least 2 gelling agents chosen from (hetero)polysaccharides, (ii) at least a foaming surfactant and (iii) an acrylic copolymer as described below as a scrub composition for the skin, preferably for the face or the body.

Hydrogel Beads

The composition according to the invention comprises hydrogel beads as scrubbing particles.

By "bead" in the sense of the present invention it is meant a solid of substantially spherical or ovoid shape.

By "hydrogel", it is meant an aqueous gel of gelling agent. In the present invention, the gelling agent is a (hetero)polysaccharide as described below.

Preferably, the hydrogel beads according to the invention have an average particle size ranging from 0.2 to 1.5 mm, preferably from 0.7 to 1.1 mm.

The hydrogel beads according to the invention comprise at least 2 gelling agents chosen from (hetero)polysaccharides.

The (hetero)polysaccharides may be chosen from polysaccharides, such as polymer of galactose obtained from red seaweeds, such as for example agarose, like agar-agar; alginic acid or alginate salts; (co)polymers of glucosamine, such as chitosan or its salts; heteropolysaccharides such as carrageenan, and mixtures thereof.

The (hetero)polysaccharides may be chosen from polysaccharides, such as polymers of galactose obtained from red seaweeds. In a particular embodiment, the (hetero)polysaccharide is chosen from agaroses, such as agar-agar. Advantageously, the average number molecular weight of this (hetero)polysaccharide is ranging from 110 000 to 160 000.

The (hetero)polysaccharides may be chosen from alginic acid or alginate salts.

Alginic acid is a natural substance extracted from brown algae or bacteria. Alginic acid is a polyuronic acid with 2 uronic acids linked by (1,4)-glycosidic bonds: β-D-mannuronic acid (M) and α-L-glucuronic acid (G).

Alginic acid forms water-soluble salts (alginates) with alkali metals, such as sodium, calcium, potassium, lithium; (C1-C8) alkylamines and (C1-C8) alkyl ammoniums such as methylamine, ethanolamine, diethanolamine, triethanolamine. These alginates are water soluble at pH=4, but dissociate in alginic acid at pH below 4.

The (hetero)polysaccharides may be chosen from (co)polymers of glucosamine such as chitosan or its salts.

Chitosan is a polyoside made of D-glucosamine and N-acetyl-D-glucosamine.

According to the invention, the beads may comprise chitosan or its salts, such as salts with carboxylic acid comprising 1 to 6 carbon atoms like acetic acid, thioglycolic acid, adipic acid, ascorbic acid, formic acid, glycolic acid and lactic acid; N-acylated chitosans; N-carboxyalkyl chitosans, N-carboxyacyl chitosans; O-carboxyalkyl chitosans; deoxyglycit-1-yl chitosans; hydroxyalkyl chitosans The (hetero)polysaccharides may be chosen from heteropolysaccharides such as carrageenan.

Carrageenans are sulfated polysaccharides which constitute the cell walls of various red algae, from which they may be obtained. Among these red algae mention may be made in a nonlimiting manner of *Kappaphycus alvarezii, Eucheuma denticulatum, Eucheuma spinosum, Chondrus crispus, Betaphycus gelatinum, Gigartina skottsbergii, Gigartina canaliculata, Sarcothalia crispata, Mazzaella laminaroides, Hypnea musciformis, Mastocarpus stellatus* and *Iridaea cordata*.

Carrageenans comprise long galactan chains formed by disaccharide units. These polysaccharides are composed of an alternation of (1→3) β-D-galactopyranose (G unit) and (1→4) α-galactopyranose (D unit) or 3,6-anhydro-α-galactopyranose (AnGal unit). Each sugar unit may be sulfated one or more times in position 2, 3, 4 or 6. Methyl and pyruvic acid groups may also be found, along with other sugar units grafted onto the base structures described previously. Carrageenans were initially subdivided into subfamilies as a function of their solubility in KCl and then according to the number and position of the sulfate groups and the presence of 3',6'-anhydro bridges on the galactopyranosyl residues. At least 15 carrageenans are listed, the structure of which depends on the alga of origin and on the extraction method. Among the most common, mention may be made of the following carrageenans: μ-carrageenan ((1→3) β-D-galactopyranose-4-sulfate-(1→4)-α-D-galactopyranose-6-sulfate), κ-carrageenan ((1→3) β-D-galactopyranose-4-sulfate-(1→4) 3,6-anhydro-α-D-galactopyranose), ν-carrageenan ((1→3) β-D-galactopyranose-4-sulfate-(1→4)-α-D-galactopyranose-2,6-disulfate), τ-carrageenan ((1→3) β-D-galactopyranose-4-sulfate-(1→4) 3,6-anhydro-α-D-galactopyranose-2-sulfatesulfate)), λ-carrageenan ((1→3) β-D-galactopyranose-2-sulfate-(1→4)-α-D-galactopyranose-2,6-disulfate), θ-carrageenan ((1→3) β-D-galactopyranose-2-sulfate-(1→4) 3,6-anhydro-α-D-galactopyranose-2-sulfate.

These carrageenans may be obtained in the form of mixtures of different structures such as, in a non-limiting manner, mixtures of the κβ, κι and κμ forms.

Carrageenans that may be used may be chosen especially from carrageenans of the μ, κ, ν, ι or λθ type, and mixtures thereof in all proportions. Carrageenans that are particularly suitable for use in the invention are carrageenans of lambda, kappa or iota form, hybrids thereof, and mixtures thereof in all proportions. Use will be made especially of carrageenans of λ form, of κ form and/or of ι form, or mixtures thereof, and in particular carrageenans derived from *Chondrus crispus* or *Kappaphycus alvarezii*.

The carrageenans of the present invention may be used in acid form or in salified form. Acceptable salts that may be mentioned in a non-limiting manner include lithium, sodium, potassium, calcium, zinc and ammonium salts or the salts obtained with an organic base counterion, such as a primary, secondary or tertiary (C1-C6) alkylamine, especially triethylamine or butylamine. This primary, secondary or tertiary alkylamine may comprise one or more nitrogen and/or oxygen atoms and may thus comprise, for example, one or more alcohol functions; mention may be made especially of amino-2-methyl-2-propanol, triethanolamine and dimethylamino-2-propanol. Mention may also be made of lysine or 3-(dimethylamino)propylamine. These sulfated polysaccharides may also comprise a mixture of counterions among those defined above in a non-limiting manner.

The molecular weight of the carrageenans that are useful for the present invention is between 300 and 100×106 daltons. Their molecular weight is preferentially between 10×103 Da and 10×106 Da.

The sulfur content of the carrageenans is preferentially between 5% and 25% (calculated on a weight basis relative to the total weight of the carrageenan) and more preferentially between 7% and 20%. Carrageenans may especially have a sulfur content from about 15% to 20%.

Carrageenans that are particularly suitable for use in the invention predominantly comprise lambda forms, or are in lambda form. The term "predominantly" means that the percentage of this type of chain in the composition of the product is greater than or equal to 50%, this proportion possibly being greater than or equal to 80% in certain embodiments. Such carrageenans may especially be extracted from *Chondrus crispus*, such as those sold by the company Cargill under the respective names Satiagum UTC 30 Carrageenan lamda Cargill and Satiagum UTC 10 Carrageenan lamda Cargill.

In a preferred embodiment, the hydrogel beads according to the inventions comprise (hetero)polysaccharide(s) in an amount ranging from 2 to 10% by weight, preferably from 3 to 8% by weight, even more preferably from 4 to 7% by weight relative to the total weight of the beads.

In a preferred embodiment, the hydrogel beads according to the invention comprise agar-agar and carrageenan. Preferably, the hydrogel beads comprise agar-agar and carrageenan in a weight ratio of agar-agar/carrageenan ranging from 1 to 1.5, and more preferably ranging from 1.2 to 1.3.

The hydrogel beads comprise water. The water content is preferably ranging from 80 to 98% by weight, preferably from 90 to 97% by weight, even more preferably from 92 to 96% by weight, relative to the total weight of the hydrogel beads.

In a particular embodiment, the hydrogel beads according to the invention may further comprise various additives, such as actives, fragrance, preservatives, water-soluble salts, and mixtures thereof.

In a particular embodiment, the hydrogel beads according to the invention are translucent.

In a particular embodiment, the hydrogel beads according to the invention are translucent when suspended in water.

The hydrogel beads according to the invention may be present in the composition in an amount ranging from 2 to 50% by weight in active material, preferably from 3 to 40% by weight in active material relative to the total weight of the composition.

The hydrogel beads according to the invention may be prepared according to the process described in U.S. Pat. No. 6,467,699 patent.

Foaming Surfactant

The composition according to the invention comprises at least one foaming surfactant.

Foaming surfactants are detergents and differ from emulsifiers in the value of their HLB (Hydrophilic-Lipophilic Balance), the HLB being the ratio of the hydrophilic part to the lipophilic part in the molecule. The term "HLB" is well known to a person skilled in the art and is described, for example, in "The HLB system. A time-saving guide to Emulsifier Selection" (published by ICI Americas Inc., 1984). For emulsifiers, the HLB generally ranges from 3 to 8 for the preparation of W/O emulsions and from 8 to 18 for the preparation of O/W emulsions, whereas foaming surfactants generally have an HLB of greater than 20.

The foaming surfactant may be present in the composition in an amount ranging from 0.5 to 20% by weight of active material, preferably from 1 to 10% by weight of active material, and more preferably from 3 to 10% by weight of active material, relative to the total weight of the composition.

The foaming surfactant may be chosen from anionic surfactants, amphoteric surfactants, non ionic surfactants and their mixtures.

Anionic Surfactants

The composition according to the invention may comprise one or more anionic surfactants.

The term anionic surfactant means a surfactant having only anionic groups as ionic or ionizable groups.

In the present description, an entity is qualified as "anionic" when it has at least one permanent negative charge or when it can be ionized by a negatively charged entity, under the conditions of use of the composition of the invention (medium, pH, for example) and containing no cationic charge.

The anionic surfactants may be sulfate(s) or sulfonate(s) which have at least one sulfate group (—OSO$_3$H or —OSO$_3$—), and/or a sulfonate group (—SO$_3$H or —SO$_3$), or else carboxylic or carboxylate surfactants having at least one carboxylic acid group (—COOH or —COO—).

It is understood that the anionic carboxylate surfactants may include one or more sulfate or sulfonate groups; sulfonate anionic surfactants may optionally further comprise one or more sulfate or carboxylate groups; and sulfate anionic surfactants may optionally further comprise one or more carboxylate or sulfonate groups.

Anionic surfactants which may be used include alkyl sulfates, alkyl ether sulfates, alkylamido ether sulfates, alkylaryl polyether sulfates, monoglyceride sulfates, alkyl sulfonates or alpha olefin sulfonates, alkylamide sulfonates, alkylarylsulfonates, paraffin sulfonates, alkyl sulfosuccinates, alkyl ether sulfosuccinates, alkylamide sulfosuccinates, alkyl sulfoacetates, acylsarcosinates, acylglutamates, alkyl sulphosuccinamates, acylisethionates and N-acyl taurates, salts of alkyl monoesters and polyglycosidepolycarboxylic acids, acyl lactylates, N-acyl glycinates, salts of D-galactoside-uronic acids, salts of alkyl ether carboxylic acids, alkyl aryl ether carboxylic acid salts, salts of alkyl amidoether carboxylic acids, sulfoacetates, sulfolaurates, and the corresponding non-salt forms all of these compounds, the alkyl and acyl groups of all these compounds containing from 6 to 40 carbon atoms, especially 14 to 30 carbon atoms, more preferably from 16 to 22 carbon atoms; and aryl means phenyl group. These compounds may be ethoxylated and then preferably comprise from 1 to 50 ethylene oxide units.

Ethylene polyoxyalkylenated (C6-C24) (amido) ether carboxylic acids and salts thereof may also be cited, in particular those comprising from 2 to 50 alkylene oxide groups, in particular, such as sold by the company KAO under the names AKYPO.

The more preferred alkyl (C6-C24) (amido) ether carboxylic acids correspond to the following formula:

$$R_1\text{---}(OC_2H_4)_n OCH_2COOA \qquad (1)$$

wherein:
R1 represents a radical or a mixture of linear or branched alkyl or alkenyl in C8-C22, a alkyl (C8-C9) phenyl radical, a $R_2CONH\text{---}CH_2\text{---}CH_2\text{---}$ group with $R_2$ denoting an alkyl radical linear or branched alkenyl in C9-C21; preferably $R_1$ being an alkyl radical having 8 to 20 carbon atoms, preferably from 8 to 18 carbon atoms and aryl preferably denoting phenyl,
n is an integer or decimal number (average value) which may vary from 2 to 24 and preferably 2 to 10,
A denotes H, ammonium, Na, K, Li, Mg or monoethanolamine or triethanolamine.

It is also possible to use mixtures of compounds of formula (1), in particular mixtures in which the R1 groups differ.

Polyoxyalkylenated (C6-C24) (amido) ether carboxylic acids preferably used in the present invention are selected from those of formula (1) wherein:
R1 denotes a radical or a mixture of (C12-C14)alkyl radicals, cocoyl, oleyl, a nonyl or octylphenyl radical,
A denotes hydrogen or sodium, and
n is from 2 to 20 and preferably 2 to 10.

Polyoxy(C6-C24)alkylenated ether carboxylic acids and their salts are preferably used, and also polyoxyalkylenated (C6-C24)alkylamido ether carboxylic acids and salts thereof; in particular those having from 2 to 15 alkylene oxide groups.

Even more preferably, one can use the compounds of formula (1) wherein R is a C12 alkyl radical, A denotes hydrogen or sodium and n is from 2 to 10.

Salts are especially selected from alkali metal salts, especially sodium, ammonium salts, amine salts, amino alcohol such as triethanolamine or monoethanolamine, and magnesium salts.

Preferably, the anionic surfactants are chosen among, alone or as a mixture:
(C6-C24)alkylsulfates, especially in C12-C20,
(C6-C24)alkyl ether sulfates, especially in C12-C20, preferably containing from 2 to 20 ethylene oxide units,
(C6-C24)alkylsulfosuccinates, especially in C12-C20, including laurylsulfosuccinates,
(C6-C24)alkyl ether sulfosuccinates, especially in C12-C20,
(C6-C24)acyl sarcosinates, especially in C12-C20, including palmitoylsarcosinates,
(C6-C24)alkyl ether carboxylates, preferably (C12-C20) alkyl ether carboxylates,
(C6-C24)acyl isethionates, preferably (C12-C18)acyl isethionates,
polyoxyalkylenated (C6-C24)alkyl (amido) ether carboxylic acids and salts thereof, in particular those comprising from 2 to 50 alkylene oxide groups, especially ethylene,
(C6-C24)acylglutamates, especially in C12-C20,
(C6-C24)acylglycinates, especially in C12-C20,
particularly in the form of alkali or alkaline earth metal, ammonium, amine or aminoalcohol.

More preferably, the anionic surfactant is chosen from (C6-C24)alkyl sulfates, (C6-C24)alkyl ether sulfates such as sodium lauryl ether sulfate, isethionates, amino acids, in particular glycinates, such as sodium N-cocoyl glycinate, their alkali salts, and mixtures thereof.

Amphoteric Surfactants

The composition according to the invention may comprise one or more amphoteric surfactants.

The amphoteric surfactants that may be used in the invention may be optionally quaternized secondary or tertiary aliphatic amine derivatives, in which the aliphatic group is a linear or branched chain comprising from 8 to 22 carbon atoms, said amine derivatives containing at least one anionic group, for instance a carboxylate, sulfonate, sulfate, phosphate or phosphonate group.

Mention may be made in particular of (C8-C20)alkylbetaines, sulfobetaines, (C8-C20)alkylsulfobetaines, (C8-C20)alkylamido(C1-C6)alkylbetaines, such as cocamidopropyl-betaine like the one sold under the trade name Dehyton PK 45 by Cognis, and (C8-C20)alkylamido(C1-C6)alkylsulfobetaines, and mixtures thereof.

Among the optionally quaternized secondary or tertiary aliphatic amine derivatives that may be used, mention may also be made of the products of respective structures (A1) and (A2) below:

$$R_a\text{---}CON(Z)CH_2\text{---}(CH_2)_m\text{---}N+(R_b)(R_c) \\ (CH_2COO^-) \qquad (A1)$$

in which:
Ra represents a C10-C30 alkyl or alkenyl group derived from an acid $R_a\text{---}COOH$ preferably present in hydrolyzed coconut oil, a heptyl group, a nonyl group or an undecyl group,
$R_b$ represents a β-hydroxyethyl group,
$R_c$ represents a carboxymethyl group;
m is equal to 0, 1 or 2,
Z represents a hydrogen atom or a hydroxyethyl or carboxymethyl group.

$$R_a\text{---}CON(Z)CH_2\text{---}(CH_2)_m\text{---}N(B)(B') \qquad (A2)$$

in which:
- B represents —CH$_2$CH$_2$OX', with X' representing —CH$_2$—COOH, CH$_2$—COOZ', CH$_2$CH$_2$—COOH, —CH$_2$CH$_2$—COOZ', or a hydrogen atom,
- B' represents —(CH$_2$)z-Y', with z=1 or 2, and Y' representing COOH, COOZ', CH$_2$—CHOH—SO$_3$H or —CH$_2$—CHOH—SO$_3$Z',
- m' is equal to 0, 1 or 2,
- Z represents a hydrogen atom or a hydroxyethyl or carboxymethyl group,
- Z' represents an ion resulting from an alkali or alkaline-earth metal, such as sodium, potassium or magnesium; an ammonium ion; or an ion resulting from an organic amine and in particular from an amino alcohol, such as monoethanolamine, diethanolamine and triethanolamine, monoisopropanolamine, diisopropanolamine or triisopropanolamine, 2-amino-2-methyl-1-propanol, 2-amino-2-methyl-1,3-propanediol and tris (hydroxymethyl)aminomethane,
- Ra' represents a C10-C30 alkyl or alkenyl group of an acid R$_a$COOH preferably present in hydrolyzed linseed oil or coconut oil, an alkyl group, in particular a C17 alkyl group, and its iso form, or an unsaturated C17 group.

The compounds corresponding to formula (A2) are preferred.

Among the compounds corresponding to formula (A2) in which X' represents a hydrogen atom, mention may be made of compounds classified in the CTFA dictionary, under the names sodium cocoamphoacetate, sodium lauroamphoacetate, sodium caproamphoacetate and sodium capryloamphoacetate.

Other compounds corresponding to formula (A2) are alkali salts of (C8-C16)alkylamphodiacetate such as disodium cocoamphodiacetate, disodium lauroamphodiacetate, disodium caproamphodiacetate, disodium capryloamphodiacetate, alkali salts of (C8-C16)alkylamphodipropionate such as disodium cocoamphodipropionate, disodium lauroamphodipropionate, disodium caproamphodipropionate, disodium capryloamphodipropionate, (C8-C16)alkylamphodipropionic acids such as lauroamphodipropionic acid and cocoamphodipropionic acid.

Examples that may be mentioned include the cocoamphodiacetate sold by the company Rhodia under the trade name Miranol® C2M Concentrate, the sodium cocoamphoacetate sold under the trade name Miranol Ultra C 32 and the product sold by the company Chimex under the trade name Chimexane HA.

Use may also be made of the compounds of formula (A3):

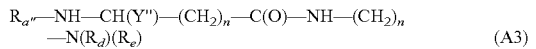

(A3)

in which:
- R$_a$″ represents a C10-C30 alkyl or alkenyl group of an acid R$_a$″—C(O)OH preferably present in hydrolyzed linseed oil or coconut oil;
- Y″ represents the group —C(O)OH, —C(O)OZ″, —CH$_2$—CH(OH)—SO$_3$H or the group CH$_2$—CH(OH)—SO$_3$—Z″, with Z″ representing a cationic counterion resulting from an alkali metal or alkaline-earth metal, such as sodium, an ammonium ion or an ion resulting from an organic amine;
- R$_d$ and R$_e$ represent, independently of each other, a C1-C4 alkyl or hydroxyalkyl radical; and
- n and n' denote, independently of each other, an integer ranging from 1 to 3.

Among the compounds corresponding to formula (A3), mention may in particular be made of the compound classified in the CTFA dictionary under the name sodium diethylaminopropyl cocoaspartamide, such as the one sold by the company Chimex under the name Chimexane HB.

Preferably, the amphoteric surfactants are chosen from (C8-C20)alkylbetaines, (C8-C20)alkylamido(C1-C6)alkylbetaines, (C8-C20)alkylamphoacetates and (C8-C20)alkylamphodiacetates, and mixtures thereof.

Non Ionic Surfactants

The composition may comprise one or more non ionic surfactant, preferably alkylpolyglycoside surfactants, especially represented by formula (I):

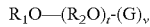

wherein:
- R$_1$ represents a linear or branched alkyl or alkenyl radical having 6 to 24 carbon atoms, especially 8 to 18 carbon atoms, or an alkylphenyl radical whose linear or branched alkyl radical comprises from 6 to 24 carbon atoms, especially 8 to 18 carbon atoms,
- R$_2$ represents an alkylene radical having 2 to 4 carbon atoms,
- G is a sugar unit containing 5 to 6 carbon atoms,
- t is a value ranging from 0 to 10, preferably from 0 to 4,
- v is a value ranging from 1 to 15, preferably from 1 to 4.

Preferably, the alkylpolyglycoside surfactants are compounds of formula (I) described above wherein:
- R$_1$ denotes a linear or branched saturated or unsaturated alkyl radical having 8 to 18 carbon atoms,
- R$_2$ represents an alkylene radical having 2 to 4 carbon atoms,
- t is a value ranging from 0 to 3, preferably equal to 0,
- G denotes glucose, fructose or galactose, preferably glucose,
- the degree of polymerization, i.e. the value of v, may range from 1 to 15, preferably from 1 to 4; the average degree of polymerization is more particularly between 1 and 2.

Glycosidic linkages between the sugar units are generally 1-6 or 1-4, preferably 1-4.

Preferably, the alkylpolyglycoside surfactant is an alkylpolyglucoside surfactant, even more preferably a C8-C16 alkylpolyglucoside, and particularly preferably chosen among decylglucoside, caprylyl/capryl glucoside, laurylglucoside, cocoylglucoside, caprylylglucoside, and mixtures thereof.

Among the commercial products, the following product may be cited: products sold by COGNIS under the names PLANTAREN® (600 CS/U, 1200 and 2000) or PLANTACARE® (818, 1200 and 2000); products sold by SEPPIC under the names ORAMIX® CG 110 and ORAMIX® NS 10; products sold by BASF under the name LUTENSOL GD 70; products sold by the company CHEM Y under the name AG10 LK; or products sold under the trade name MYDOL 10 by KAO.

Preferably, a C8-C16 alkylpolyglucoside is used, in particular chosen from decylglucoside, caprylyl/capryl glucoside, laurylglucoside, cocoylglucoside, caprylylglucoside, and mixtures thereof.

Acrylic Copolymer

The composition according to the invention comprises an acrylic copolymer.

The acrylic copolymer used in the composition of the invention is chosen from copolymers resulting from the polymerization of at least one monomer (a) chosen from carboxylic acids comprising a α,β-ethylenic insaturation or their esters as defined hereafter, with at least one monomer (b) comprising an ethylenic insaturation with a hydrophobic group having a saturated or unsaturated and linear or branched hydrocarbon chain comprising at least 8 carbon atoms, preferably from 10 to 30 carbon atoms.

In a particular embodiment, the acrylic copolymer is anionic.

The term "copolymers" is understood to mean both copolymers obtained from two types of monomers and those obtained from more than two types of monomers, such as terpolymers obtained from three types of monomers.

The chemical structure of the acrylic copolymer comprises at least one hydrophilic unit and at least one hydrophobic unit. The term "hydrophobic group" or "hydrophobic unit" is intended to mean a radical possessing a saturated or unsaturated and linear or branched hydrocarbon chain comprising at least 8 carbon atoms, preferably from 10 to 30 carbon atoms, in particular from 12 to 30 carbon atoms and more preferably from 18 to 30 carbon atoms.

Preferably, the acrylic copolymers are chosen from copolymers resulting from the polymerization of:
at least one monomer of following formula (1):

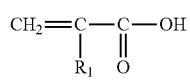
(1)

in which $R_1$ denotes H or $CH_3$ or $C_2H_5$, that is to say acrylic acid, methacrylic acid or ethacrylic acid monomers, and at least one monomer of unsaturated carboxylic acid $(C_{10}-C_{30})$alkyl ester which corresponds to the monomer of following formula (2):

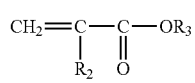
(2)

in which $R_2$ denotes H or $CH_3$ or $C_2H_5$ (that is to say, acrylate, methacrylate or ethacrylate units) and preferably H (acrylate units) or $CH_3$ (methacrylate units) and $R_3$ denotes a $C_{10}-C_{30}$ and preferably $C_{12}-C_{22}$ alkyl radical.

The $(C_{10}-C_{30})$alkyl esters of unsaturated carboxylic acids are preferably chosen among lauryl acrylate, stearyl acrylate, decyl acrylate, isodecyl acrylate, dodecyl acrylate and the corresponding methacrylates, such as lauryl methacrylate, stearyl methacrylate, decyl methacrylate, isodecyl methacrylate and dodecyl methacrylate, and their mixtures, and preferably lauryl acrylate, stearyl acrylate, decyl acrylate, isodecyl acrylate, dodecyl acrylate, and mixtures thereof.

According to a preferred embodiment, these acrylic copolymers are crosslinked.

Such anionic polymers are described and prepared, for example, according to U.S. Pat. Nos. 3,915,921 and 4,509,949.

In a particular embodiment, the acrylic copolymer is chosen among copolymers resulting from the polymerization of a mixture of monomers comprising:
(i) acrylic acid,
(ii) an ester of formula (2) described above in which $R_2$ denotes H or $CH_3$ and $R_3$ denotes an alkyl radical having from 10 to 30 carbon atoms, and (iii) a crosslinking agent which is a copolymerizable polyethylenic unsaturated monomer, such as diallyl phthalate, allyl (meth)acrylate, divinylbenzene, (poly)ethylene glycol dimethacrylate, methylenebisacrylamide, allyl ether of sucrose or an allyl ether of pentaerythritol.

Use will more particularly be made, among copolymers of this type, of those composed of 95 to 60% by weight of acrylic acid (hydrophilic unit), 4 to 40% by weight of $C_{10}-C_{30}$ alkyl acrylate (hydrophobic unit) and 0 to 6% by weight of crosslinking polymerizable monomer or else of those composed of 98 to 96% by weight of acrylic acid (hydrophilic unit), 1 to 4% by weight of $C_{10}-C_{30}$ alkyl acrylate (hydrophobic unit) and 0.1 to 0.6% by weight of crosslinking polymerizable monomer, such as those described above.

The polymers according to the invention are preferably partially or completely neutralized by a mineral base such as, for example, an alkali metal base like sodium hydroxide and potassium hydroxide, or ammonium hydroxide, or by an organic base such as mono-, di- and triethanolamine, aminomethylpropanediol, N methyl¬glucamine, basic amino acids such as arginine and lysine, and mixtures thereof.

In the sense of the present invention, "partially neutralized" is to be understood as at least 70% by weight being neutralized, preferably 80% by weight.

In a particular embodiment, the optimum neutralization is achieved when the pH is ranging from 5 to 7.

Among acrylic copolymers that may be used according to the invention, preference is very particularly given to acrylic acid/$C_{10}-C_{30}$ alkyl acrylate copolymers (INCI name: Acrylates/C10-30 Alkyl Acrylate Crosspolymer), such as the products sold by Lubrizol under the trade names Pemulen TR1, Pemulen TR2, Carbopol 1382, Carbopol EDT 2020, Carbopol Ultrez 20 and more preferably Carbopol Ultrez 20, Carbopol EDT 2020, and mixtures thereof.

The acrylic copolymer may be present in the composition according to the invention in an amount ranging from 0.1 to 5% by weight of active material, preferably from 0.2 to 2% by weight of active material, and more preferably from 0.5 to 1.5% by weight of active material, relative to the total weight of the composition.

Silica

The composition according to the invention may also comprise silica.

In a particular embodiment, the silica used in the composition of the invention is translucent when suspended in an aqueous solution.

In a preferred embodiment, the average particle size of silica particles is of less than or equal to 500 microns, preferably ranging from 100 μm to 500 μm.

The silica particle may be of any shape, such as lamellar shape, spherical shape, or in the form of fibers.

In the present invention, the expression "spherical particles" means particles which have the shape or substantially the shape of a sphere and which are insoluble in the medium of the composition of the invention.

The expression "lamellar particles" is to be understood in the present invention as particles of parallelepipedal shape (rectangular or square surface), discoid shape (circular surface) or ellipsoid shape (oval surface) characterized by three dimensions: a length, a width and a height.

In a particular embodiment, the composition according to the invention comprises silica chosen from silica powder, preferably amorphous silica, like the one sold under the trade name Sorbosil BFG 50 by PQ Corporation.

Silica may be present in the composition according to the invention in an amount ranging from 0.1 to 3% by weight of active material relative to the total weight of the composition.

Aqueous Phase

The composition according to the invention comprises water. The amount of water in the composition may be ranging from 30 to 99% by weight, preferably ranging from 35 to 99% by weight, more preferably ranging from 50 to 95% by weight, and even more preferably from 70 to 90% by weight, relative to the total weight of the composition.

The composition may comprise at least one solvent that is water-soluble at room temperature (25° C.), such as for example linear or branched monoalcohol with 2 to 6 carbon atoms, like ethanol, propanol, butanol, isopropanol, isobutanol; polyols with 2 to 20 carbon atoms, preferably 2 to 6 carbon atoms, like glycerine, propylene glycol, isoprene glycol, butylene glycol, pentylene glycol, hexylene glycol, propylene glycol, glycerol, sorbitol, polyethylene glycols, polypropylene glycols, and their mixtures. The water-soluble organic solvent may be present in the composition in an amount ranging from 0.05 to 20% by weight, preferably ranging from 0.1 to 15% by weight, relative to the total weight of the composition.

Additives or Optional Ingredients

The composition according to the invention may comprise various additives, preferably water-soluble additives, chosen from those conventionally used in cleansing, scrubbing, skin care or make-up removal products.

The composition according to the invention may thus comprise one or more of the following additives: viscosity adjuster, antibacterial agents, preserving agents, sequestrants, antioxidants, fragrances or perfumes, dyestuffs, thickening polymers, color stabilizer.

The composition according to the invention may also comprise a neutralizer, such as C2-C6-alkanolamine like triethanolamine, alkali hydroxides like sodium hydroxide and potassium hydroxide, and mixtures thereof.

The amounts of these adjuvants are those conventionally in the field under consideration, for example from 0.01% to 10% of the total weight of the composition.

The composition of the invention is a cosmetic composition.

The scrub composition according to the invention is aqueous, preferably under the form of a gel.

In a preferred embodiment, the composition of the invention has a viscosity at 25° C. ranging from 2.2 to 7 Pa·s, preferably ranging from 2.5 to 5 Pa·s.

In the framework of the present invention, the viscosity measurements are performed at 25° C. and atmospheric pressure using a Rheomat RM180® apparatus. The sample is brought at the temperature of 25° C.±0.5° C. The viscosity is measured using mobile 3 attachment to Rheomat RM180® at a rotation speed of 200 (fixed) after rotation of the measuring instrument for 10 minutes. The corresponding value in UD (unit deflection) is converted to Pa·s.

In a preferred embodiment, the composition has a clear and/or translucent appearance (visual observation). In a particular embodiment, the scrubbing particles are not distinctly visible in the scrubbing composition.

In an embodiment, the pH of the cleansing scrubbing composition is ranging from 5 to 7.

Preparation of the Composition

The composition according to the invention is prepared according to a procedure that comprises the following steps.

The acrylic copolymer is dispersed in water.

The aqueous dispersion of acrylic copolymer is heated at a temperature of 60-70° C., preferably of 65° C.

Additives, if present, are added to the aqueous composition of acrylic copolymer.

Foaming surfactants are added at a temperature of 60-65° C.

Neutralizing agent, if present, is added at a temperature of 55-65° C.

Hydrogel beads are added under stirring to the composition.

Use of the Composition

The invention also relates to the use of composition comprising, in aqueous medium, beads comprising at least 2 gelling agent chosen from (hetero)polysaccharides, at least a foaming surfactant and an acrylic copolymer as described previously as a scrub composition for the skin, preferably for the face or the body.

The invention further relates to a process for cleansing the skin, preferably the face or the body, comprising applying a composition comprising, in an aqueous medium, beads comprising at least 2 gelling agent chosen from (hetero)polysaccharides, at least a foaming surfactant and an acrylic copolymer as described previously.

In a first embodiment of the process for cleansing the skin, the composition is mixed with water and then the mixture is applied to dry skin, which is massaged. Advantageously, the skin id then rinsed off and preferably with water.

In a second embodiment of the process for cleansing the skin, the composition according to the invention is applied to wet skin, then the skin on which the composition has been applied is massaged. Advantageously, the skin is finally rinsed off preferably with water.

EXAMPLES

In the following examples, the hydrogel beads according to the invention (named "beads sample" in the following examples) that are used are suspended in an aqueous solution (approx. 70% in aqueous solution) and contain the following ingredients (% given by weight relative to the total weight of the solution of suspended beads):

| | |
|---|---|
| Water | 95.027 |
| agar-agar | 2.01 |
| carageenan | 1.591 |
| phenoxyethanol | 0.659 |
| caprylyl glycol | 0.529 |
| potassium chloride | 0.1 |
| glucose | 0.084 |

These hydrogel beads were prepared according to the process described in U.S. Pat. No. 6,467,699 and have an average size of approximately 0.9 mm.

In the following examples, the compositions are prepared according to the following general procedure:
1. The polymer is dispersed in water and the temperature is raised up to 65° C., except for example 3: hydroxypropyl methyl cellulose is added at 80° C. and then allowed to cool down.
2. Additives are added (preservatives, glycerin).
3. Surfactants are added at 60-65° C.
4. Neutralizing agent, if present, is added at 55-65° C.
5. An aqueous suspension of beads is added under stirring to the composition at ambient temperature.

In the following examples, the weight percentages are given relative to the total weight of the composition. "% am" means percentage of active material.

Examples 1-4: Influence of the Nature of the Polymer 2 compositions according to the invention (examples 1 and 2) comprising a polymer from the class of crosslinked acrylic acid copolymer (Carbopol ETD 2020 and Carbopol Ultrez 20) were prepared and compared to 2 comparative compositions outside the invention (examples 3 and 4) comprising cellulosic polymers (hydroxypropyl methylcellulose and hydroxyethyl cellulose), as set forth in the table below:

| Compounds | Ex 1 | Ex 2 | Ex 3 | Ex 4 |
|---|---|---|---|---|
| Water | QSP 100 | QSP 100 | QSP 100 | QSP 100 |
| Acrylates/C10-30 alkyl acrylate crosspolymer (Carbopol ETD 2020 from Lubrizol) | 1.20 | — | — | — |
| Acrylates/C10-30 alkyl acrylate crosspolymer (90% am) (Carbopol Ultrez 20 from Lubrizol) | — | 1.33 (1.20% am) | — | — |
| Hydroxypropyl methyl cellulose (Benecel K100M from Ashland) | — | — | 1.2 | — |
| Hydroxyethyl cellulose (Natrosol 250 HHR CS from Ashland) | — | — | — | 1.2 |
| Sodium laureth sulfate (70% in water) (Galaxy LES 170 from Galaxy Surfactants) | 5 (3.5% am) | 5 (3.5% am) | 5 (3.5% am) | 5 (3.5% am) |
| Glycerin | 5 | 5 | 5 | 5 |
| Triethanolamine | 1.1 | 1.1 | — | — |
| Beads sample (70% in water) | 12 (8.4% am) | 12 (8.4% am) | 12 (8.4% am) | 12 (8.4% am) |
| Phenoxyethanol | 0.7 | 0.7 | 0.7 | 0.7 |
| TOTAL | 100 | 100 | 100 | 100 |

The texture and the visual appearance of each composition were studied after storage at 25° C. after 2 months (visual observation). The composition is considered as stable if no change in visual appearance is observed after 2 months of storage at 25° C. and if the beads remain suspended. The results are summarized in the table below:

| Formula | Observation |
|---|---|
| Ex 1 | gel texture (2.6 Pa · s), translucent, beads remain suspended after 2 months at 25° C. |
| Ex 2 | gel texture (3.8 Pa · s), translucent, beads remain suspended after 2 months at 25° C. |
| Ex 3 | liquid texture (2.12 Pa · s), translucent, beads settle in 48 h at 25° C. |
| Ex 4 | liquid texture (1.95 Pa · s), translucent, beads settle in 48 h at 25° C. |

Compositions according to the invention and comprising a crosslinked acrylate copolymer (examples 1 and 2) displayed a gel texture and the beads remain suspended after 2 months at 25° C., while compositions outside the invention comprising hydroxypropyl methyl cellulose or hydroxyethyl cellulose (examples 3 and 4) afforded a liquid texture and beads settle in 48 h.

These comparative examples show the importance of the acrylic copolymer for obtaining a gel texture and a stable suspension of the beads in the compositions.

The compositions were also applied on skin: the face was wetted then 1 g of the composition is applied on the face by massage, and finally the face is rinse-off. The cosmetic properties on usage were evaluated by 5 persons: the compositions of examples 1 and 2 according to the invention were gentle, mild and soft upon application and have no irritating effect.

Examples 5-7: Influence of the Nature of the Surfactant 3 compositions according to the invention (examples 5 to 7) and comprising various surfactants (sodium laureth sulfate, cocamidopropyl betaine, decyl glucoside) as detailed in the table below were prepared.

| Compounds | Ex 5 | Ex 6 | Ex 7 |
|---|---|---|---|
| Water | QSP 100 | QSP 100 | QSP 100 |
| Acrylates/C10-30 alkyl acrylate crosspolymer (90% am) (Carbopol Ultrez 20 from Lubrizol) | 1.3 (1.17% am) | 1.3 (1.17% am) | 1.3 (1.17% am) |
| Sodium laureth sulfate (70% in water) (Galaxy LES 170 from Galaxy Surfactants) | 5 (3.5% am) | 4.5 (3.15% am) | 4.5 (3.15% am) |
| Cocamidopropyl betaine (38% am in water) (Dehyton PK 45 from Cognis) | — | 1 (0.38% am) | — |
| Decyl glucoside (40% am in water) (Mydol 10 from Kao) | — | — | 1 (0.4% am) |
| Glycerin | 5 | 5 | 5 |
| Triethanolamine | 1.1 | 1.1 | 1.1 |
| beads sample (70% am in water) | 12 (8.4% am) | 12 (8.4% am) | 12 (8.4% am) |

-continued

| Compounds | Ex 5 | Ex 6 | Ex 7 |
|---|---|---|---|
| Phenoxyethanol | 0.7 | 0.7 | 0.7 |
| TOTAL | 100 | 100 | 100 |

The texture, the appearance and the stability of each composition were evaluated. The texture and appearance of the compositions were evaluated by visual observation at 25° C. The stability was evaluated after one month of storage at various temperatures (4° C., 37° C. and 45° C.). The composition is considered as stable if no change in visual appearance is observed after one month of storage at these temperatures and if the beads remain suspended. The results are summarized in the table below:

| Formula | Observation |
|---|---|
| Ex 5 | gel texture (3.6 Pa · s), translucent, stable |
| Ex 6 | gel texture (4 Pa · s), translucent, stable |
| Ex 7 | gel texture (3.2 Pas), translucent, stable |

All compositions had a gel texture with a clear and translucent appearance and were stable, regardless the foaming surfactant used. This shows that the texture, appearance and stability of the composition are independent from the nature of the foaming surfactant used.

The compositions were also applied on skin: the face was wetted then 1 g of the composition is applied on the face by massage, and finally the face is rinse-off. The cosmetic properties on usage were evaluated by 5 persons: All compositions were gentle, mild and soft upon application and have no irritating effect.

Examples 8-10: Influence of the Amount of Beads and Presence of Silica 3 compositions according to the invention (examples 8 to 9) comprising various amounts of beads were prepared. Compositions according to examples 8 and 9 further comprise various amount of amorphous silica.

The appearance of the compositions was evaluated by visual observation.

The stability of the compositions was evaluated after one month of storage at 4° C., 37° C. and 45° C. The composition is considered as stable if no change in visual appearance is observed after one month of storage at these temperatures and if the beads remain suspended.

The compositions were also applied on skin: the face was wetted, then 1 g of the composition is applied on the face by massage, and finally the face is rinse-off. The cosmetic properties on usage were evaluated by 5 persons. The results are summarized in the table below:

| Formula | Observation |
|---|---|
| Ex 8 | gel texture (3.2 Pa · s), clear and translucent, stable, pleasant on application, non-tacky, clean and fresh feel after use, scrubbing effect enhanced |
| Ex 9 | gel texture (3.1 Pa · s), clear and translucent, stable, pleasant on application, non-tacky, clean and fresh feel after use, scrubbing effect enhanced |
| Ex 10 | gel texture (3.7 Pa · s), clear and translucent, stable, pleasant on application, non-tacky, clean and fresh feel after use |

In all cases, the compositions were clear and translucent, stable, pleasant on application (gentle, mild and soft upon application and have no irritating effect), non-tacky and leaves a clean and fresh feeling after use. When the composition further comprises amorphous silica (0.16% or 0.8% by weight of active material—examples 8 and 9), the scrubbing effect is enhanced compared to the same composition without amorphous silica (example 10).

| Compounds | Ex 8 | Ex 9 | Ex 10 |
|---|---|---|---|
| Water | QSP 100 | QSP 100 | QSP 100 |
| Acrylates/C10-30 alkyl acrylate crosspolymer (90% am) (Carbopol Ultrez 20 from Lubrizol) | 1.3 (1.17% am) | 1.3 (1.17% am) | 1.1 (0.99% am) |
| Sodium laureth sulfate (70% in water) (Galaxy LES 170 from Galaxy Surfactants) | 5 (3.5% am) | 5 (3.5% am) | 5 (3.5% am) |
| Decyl glucoside (53% in water) (Mydol 10 from Kao) | 4 (2.12% am) | 4 (2.12% am) | 4 (2.12% am) |
| Glycerin | 5 | 5 | 5 |
| Triethanolamine | 1.1 | 1.1 | 1 |
| beads sample (70% am in water) | 6 (4.2% ma) | 15 (10.5% ma) | 50 (35% ma) |
| Amorphous Silica (Sorbosil BFG 50 from PQ Corporation) | 0.2 (0.16% am) | 1 (0.8% am) | — |
| Phenoxyethanol | 0.7 | 0.7 | 0.7 |
| TOTAL | 100 | 100 | 100 |

Example 11: Influence of the Nature of the Hydrogel Beads

The following composition comprising Captivates GL7657® beads from Ashland was prepared.

| Compounds | Ex 11 |
|---|---|
| Water | QSP 100 |
| Acrylates/C10-30 alkyl acrylate crosspolymer (90% am) (Carbopol Ultrez 20 from Lubrizol) | 1.30 |
| Sodium laureth sulfate (70% in water) (Galaxy LES 170 from Galaxy Surfactants) | 5 (3.5% am) |
| Decyl glucoside (53% in water) (Plantacare 200 UP from Cognis) | 4 (2.12% am) |
| Glycerin | 5 |
| Triethanolamine | 1.1 |
| Captivates GL7657 ® beads from Ashland | 6 (4.2% am) |
| Amorphous silica Silica (Sorbosil BFG 50 from PQ Corporation) | 0.2 (0.16% am) |
| Phenoxyethanol | 0.7 |
| TOTAL | 100 |

The appearance of the composition was evaluated by visual observation.

The stability of the compositions was evaluated after one month of storage at 4° C., 37° C. and 45° C. The composition is considered as stable if no change in visual appearance is observed after one month of storage at these temperatures and if the beads remain suspended.

The compositions were also applied on skin: the face was wetted, then 1 g of the composition is applied on the face by massage, and finally the face is rinse-off. The cosmetic properties on usage were evaluated by 5 persons.

The composition had a gel texture (viscosity of 3.2 Pa·s), and was translucent and stable.

The composition was non-tacky and pleasant on application, and left a clean and fresh feeling after use.

The invention claimed is:

1. Cleansing scrub composition comprising in an aqueous medium (i) at least hydrogel beads comprising at least 2 gelling agents chosen from (hetero)polysaccharides, wherein the (hetero)polysaccharides are selected from the group consisting of agarose, alginic acid or alginate salts, (co)polymers of glucosamine, carrageenan, and mixtures thereof and wherein the average particle size of the hydrogel beads ranges from 0.2 to 1.5 mm; (ii) at least one foaming surfactant, and (iii) at least an acrylic copolymer chosen from the copolymers resulting from the polymerization of:

a. at least one monomer of formula (1):

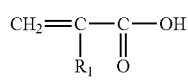

(1)

in which $R_1$ denotes H or $CH_3$ or $C_2H_5$, that is to say acrylic acid, methacrylic acid or ethacrylic acid monomers, and b. at least one monomer of unsaturated carboxylic acid $(C_{10}-C_{30})$alkyl ester which corresponds to the monomer of following formula (2):

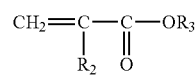

(2)

in which $R_2$ denotes H or $CH_3$ or $C_2H_5$ and $R_3$ denotes a $C_{10}-C_{30}$ alkyl radical, wherein the composition comprises water in an amount of from 50 to 95% by weight relative to the total weight of the composition.

2. Composition according to claim 1, wherein the hydrogel beads comprise agar-agar and carrageenan.

3. Composition according to claim 2, wherein agar-agar and carrageenan are present in a weight ratio of agar-agar/carrageenan ranging from 1 to 1.5.

4. Composition according to claim 1, wherein the average particle size of the hydrogel beads may range from 0.7 to 1.1 mm.

5. Composition according to claim 1, wherein the hydrogel beads are present in an amount ranging from 2 to 50% by weight of active material relative to the total weight of the composition.

6. Composition according to claim 1, wherein the foaming surfactant is an anionic surfactant preferably chosen from (C6-C40)alkyl sulfates, (C6-C40)alkyl ether sulfates, (C6-C40)alkylamido ether sulfates, (C6-C40)alkylaryl polyether sulfates, monoglyceride sulfates, (C6-C40)alkyl sulfonates or alpha olefin sulfonates, (C6-C40)alkylamide sulfonates, (C6-C40)alkylarylsulfonates, paraffin sulfonates, (C6-C40) alkyl sulfosuccinates, (C6-C40)alkyl ether sulfosuccinates, (C6-C40)alkylamide sulfosuccinates, (C6-C40)alkyl sulfoacetates, (C6-C40)acylsarcosinates, (C6-C40)acylglutamates, (C6-C40)alkyl sulphosuccinamates, (C6-C40)acylisethionates and N—(C6-C40)acyl taurates, salts of (C6-C40)alkyl monoesters and polyglycosidepolycarboxylic acids, (C6-C40)acyl lactylates, N—(C6-C40)acyl glycinates, salts of D-galactoside-uronic acids, salts of (C6-C40) alkyl ether carboxylic acids, (C6-C40)alkyl aryl ether carboxylic acid salts, salts of (C6-C40)alkyl amidoether carboxylic acids, sulfoacetates, sulfolaurates, and the corresponding non-salt forms all of these compounds; an amphoteric surfactant preferably chosen from (C8-C20)alkylbetaines, sulfobetaines, (C8-C20)alkylsulfobetaines, (C8-C20)alkylamido(C1-C6)alkylbetaines, (C8-C20)alkylamido(C1-C6)alkylsulfobetaines, alkali salts of (C8-C16) alkylamphodiacetate, alkali salts of (C8-C16) alkylamphodipropionate, (C8-C16)alkylamphodipropionic acids, and mixtures thereof; a non ionic surfactant preferably chosen from alkylpolyglycoside surfactants; or a mixture thereof.

7. Composition according to claim 1, wherein the foaming surfactant is chosen from an anionic surfactant chosen from (C6-C24)alkyl sulfates, (C6-C24)alkyl ether sulfates, isethionates, amino acids, their alkali salts, and mixtures thereof; an amphoteric surfactant chosen from (C8-C20) alkylbetaines, (C8-C20)alkylamido(C1-C6)alkylbetaines, (C8-C20)alkylamphoacetates and (C8-C20)alkylamphodiacetates, and mixtures thereof; a non ionic surfactant chosen from C8-C16 alkylpolyglucosides; and mixtures thereof.

8. Composition according to claim 1, wherein the foaming surfactant is present in an amount ranging from 1 to 10% by weight of active material relative to the total weight of the composition.

9. Composition according to claim 1, wherein the acrylic copolymer is chosen from the copolymers resulting from the polymerization of at least one monomer of formula (1) with at least one monomer of formula (2) in which $R_2$ denotes H or $CH_3$ and $R_3$ denotes a $C_{12}$-$C_{22}$ alkyl radical.

10. Composition according to claim 9, wherein the acrylic copolymer is chosen among copolymer resulting from the polymerization of a mixture of monomers comprising:
   a. acrylic acid
   b. an ester of formula (2) described above in which $R_2$ denotes H or $CH_3$ and $R_3$ denotes an alkyl radical having from 12 to 22 carbon atoms, and
   c. a crosslinking agent which is chosen among diallyl phthalate, allyl (meth)acrylate, divinylbenzene, (poly) ethylene glycol dimethacrylate, methylenebisacrylamide, allyl ether of sucrose or an allyl ether of pentaerythritol.

11. Composition according to claim 1, wherein the acrylic copolymer is present in an amount ranging from 0.1 to 5% by weight of active material relative to the total weight of the composition.

12. Composition according to claim 1, further comprising silica.

13. Composition according to claim 12, wherein the average particle size of silica is ranging from 100 μm to 500 μm.

14. Composition according to claim 1, wherein the composition is in the form of a gel.

15. Composition according to claim 1, wherein the composition has a viscosity at 25° C. ranging from 2.2 to 7 Pa·s.

16. Process for cleansing the skin, comprising applying to the skin a composition comprising in an aqueous medium (i) at least hydrogel beads comprising at least 2 gelling agents chosen from (hetero)polysaccharides, wherein the (hetero) polysaccharides are selected from agarose, alginic acid or alginate salts, (co)polymers of glucosamine, carrageenan, and mixtures thereof and wherein the average particle size of the hydrogel beads ranges from 0.2 to 1.5 mm, (ii) at least one foaming surfactant, and (iii) at least an acrylic copolymer chosen from the copolymers resulting from the polymerization of:
   a. at least one monomer of formula (1):

in which $R_1$ denotes H or $CH_3$ or $C_2H_5$, that is to say acrylic acid, methacrylic acid or ethacrylic acid monomers, and
   b. at least one monomer of unsaturated carboxylic acid ($C_{10}$-$C_{30}$)alkyl ester which corresponds to the monomer of following formula (2):

in which $R_2$ denotes H or $CH_3$ or $C_2H_5$ and $R_3$ denotes a $C_{10}$-$C_{30}$ alkyl radical
wherein the composition comprises water in an amount of from 50 to 95% by weight relative to the total weight of the composition.

* * * * *